US00PP30482P3

(12) United States Plant Patent
Suphachadiwong

(10) Patent No.: US PP30,482 P3
(45) Date of Patent: May 7, 2019

(54) ***VANDA* PLANT NAMED 'SPCDW1701'**

(50) Latin Name: ***Vanda* spp. Jones ex R. Br.**
Varietal Denomination: SPCDW1701

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/932,466

(22) Filed: Mar. 1, 2018

(65) Prior Publication Data

US 2018/0255686 P1 Sep. 6, 2018

(30) Foreign Application Priority Data

Mar. 1, 2017 (QZ) ..... PBR 2017/0650

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — Samuel R. McCoy, Jr.

(57) ABSTRACT

A new and distinct variety of *Vanda* plant named 'SPCDW1701' which is characterized by large outward-facing flowers that sit above the foliage, bright orange flower petals and sepals which are finely dotted with greyed-orange, a bright orange labellum and column, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1701'.

CROSS REFERENCE TO RELATED APPLICATIONS

This application claims priority to the Community Plant Variety Rights application number 2017/0650, filed Mar. 1, 2017, which is herein incorporated by reference.

BACKGROUND OF THE INVENTION

Parentage: The *Vanda* variety 'SPCDW1701' is the result of a planned breeding program. The new variety originated as a seedling from the crossing of *Vanda* 'BG' (not patented), the seed parent, with *Vanda* 'PK4' (not patented), the pollen parent. Both parents were developed by, and are owned by, the inventor and were never commercially released. The crossing was made by the inventor in his research greenhouse in Bangphra, Thailand in December of 2005.

The new variety was first selected in July of 2010, in a research greenhouse in Bangphra, Thailand belonging to the inventor. After identifying the new variety as a potentially interesting selection, the inventor continued confidential testing and propagation of 'SPCDW1701', assessing stability of the unique characteristics of this variety.

Asexual Reproduction: Asexual reproduction of the new cultivar 'SPCDW1701', by way of mericloning, was first initiated in January of 2011 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1701' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1701'. These characteristics in combination distinguish 'SPCDW1701' as a new and distinct *Vanda* cultivar:

1. *Vanda* 'SPCDW1701' exhibits large outward-facing flowers that sit above the foliage; and
2. *Vanda* 'SPCDW1701' exhibits bright orange flower petals and sepals which are finely dotted with greyed-orange; and
3. *Vanda* 'SPCDW1701' exhibits a bright orange labellum and column.

BOTANICAL DESCRIPTION OF THE PLANT

Figure 1:
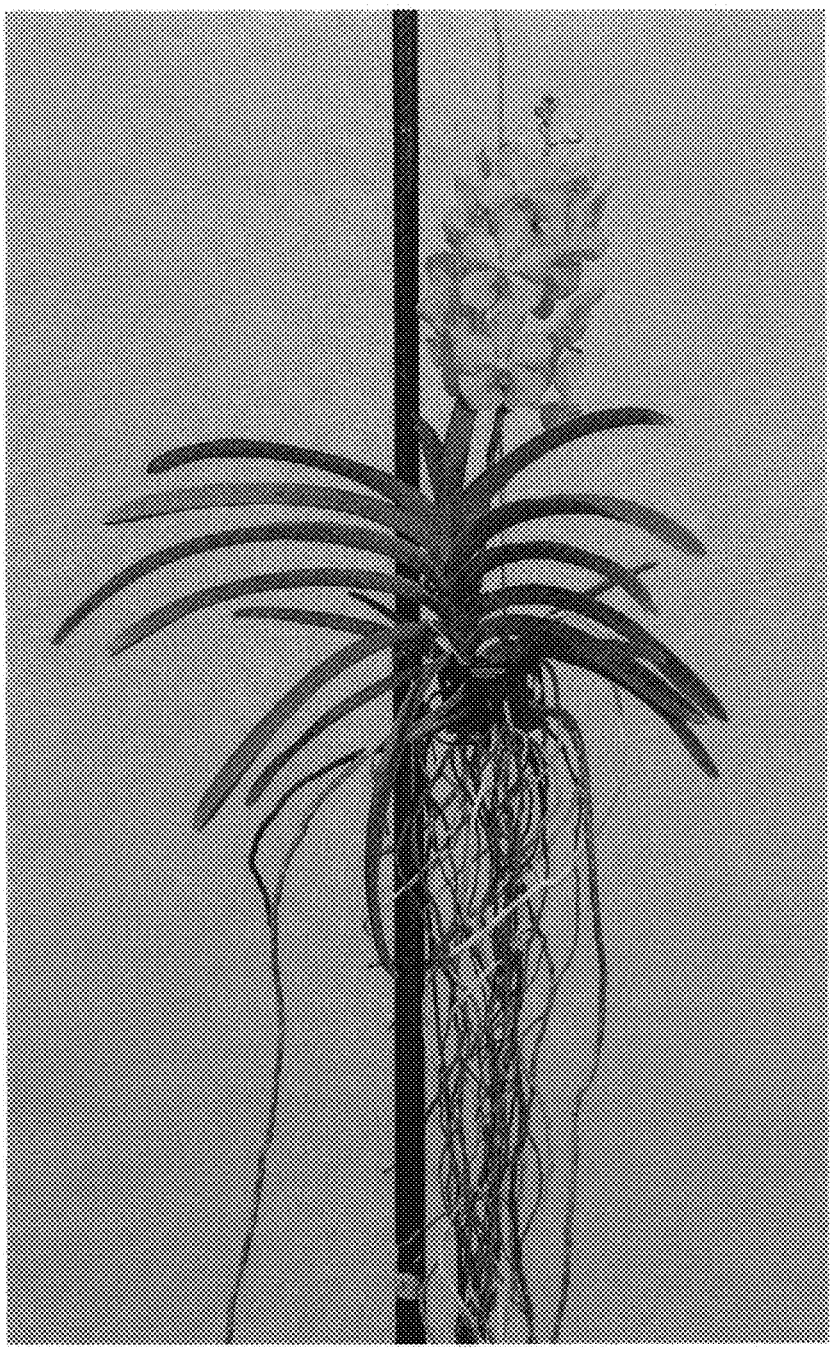
FIG. 1 illustrates, as nearly true as it is reasonably possible to make the same in color photographs of this type, an exemplary plant of 'SPCDW1701' grown in a commercial greenhouse in Honselersdijk, the Netherlands. This plant is approximately 6 years old from the time of mericloning, shown planted in an 8 by 2 cm container.
Figure 2:
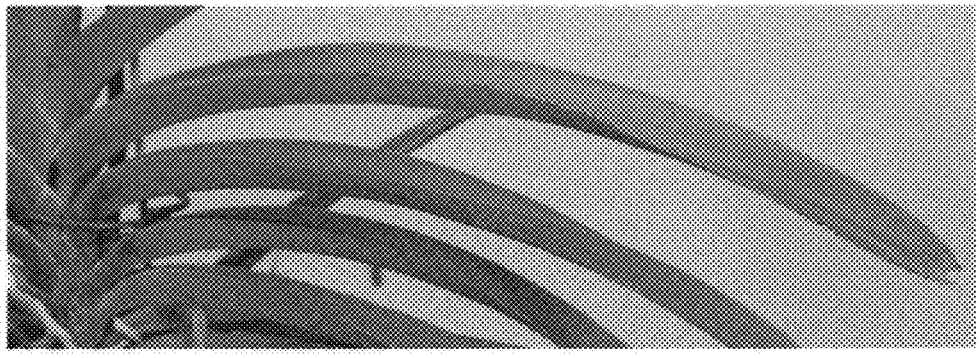
FIG. 2 illustrates, as nearly true as it is reasonably possible to make the same in color photographs of this type, the typical foliage of 'SPCDW1701'.
Figure 3:
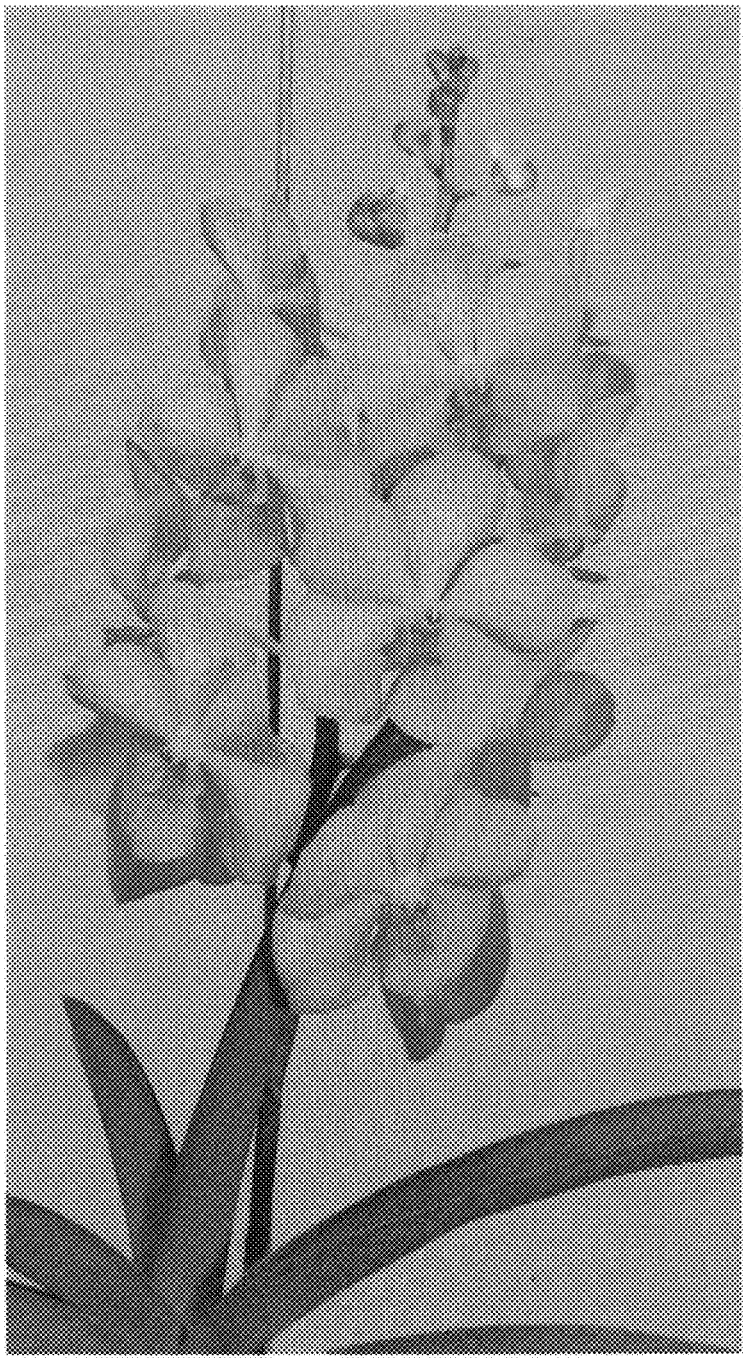
FIG. 3 illustrates, as nearly true as it is reasonably possible to make the same in color photographs of this type, the typical inflorescence of 'SPCDW1701'.
Figure 4:
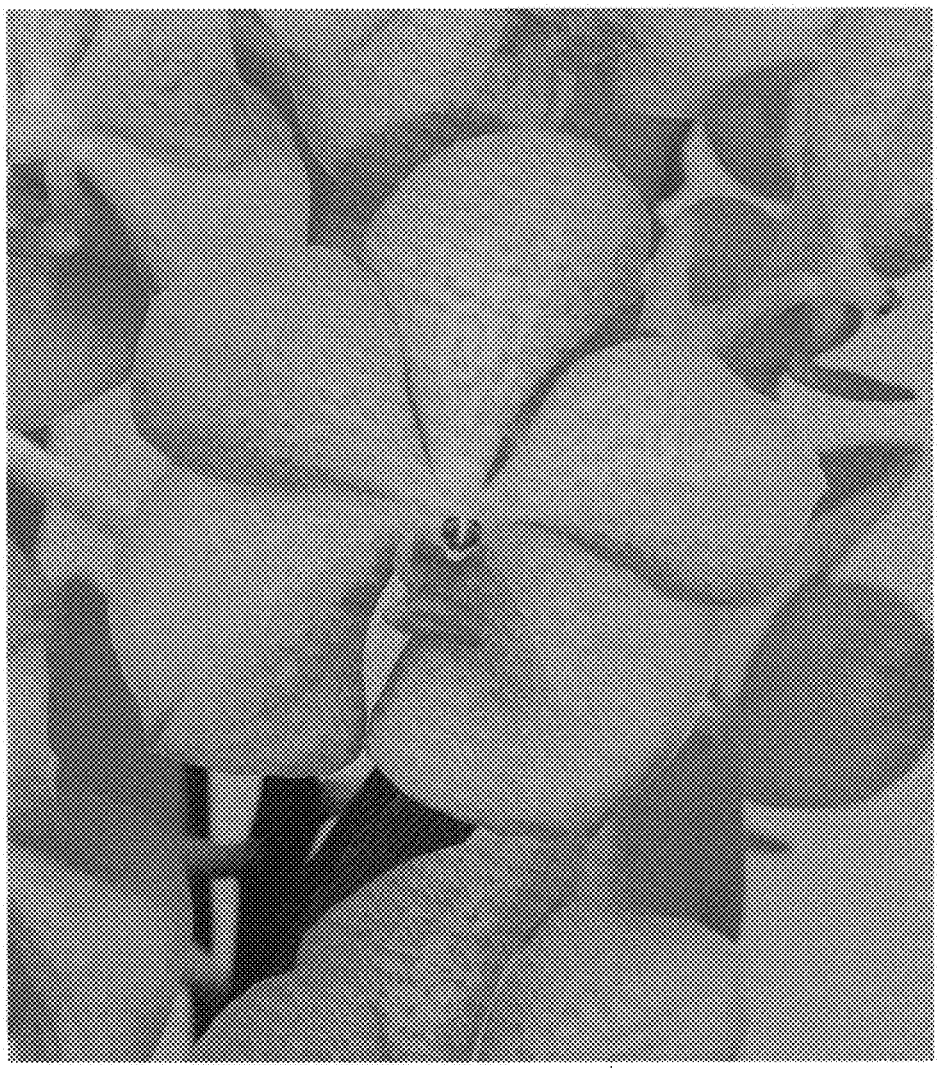
FIG. 4 illustrates, as nearly true as it is reasonably possible to make the same in color photographs of this type, the typical flower of 'SPCDW1701'.

The following observations and measurements made in January of 2018 describe averages from a sample set of six specimens of six year-old 'SPCDW1701' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1701' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1701' and comparisons with the parents and most similar commercial variety of *Vanda* are provided below.

Plant description:

*Growth habit*.—Perennial; monopodial, upright. Single monopodial leafy stem, with flowers carried slightly above the leaf plane; inflorescences growing from the leaf axils.

*Average height from base (plant grown in hanging basket, so no soil line present) to foliar plane*.—24.2 cm.

*Average height from base (plant grown in hanging basket, so no soil line present) to top of floral plane*.—36.5 cm.

*Plant spread*.—Average of 34.6 cm.

*Appropriate container size*.—8 cm by 2 cm rectangular hanging basket.

*Growth rate*.—Moderate.

*Plant vigor*.—Moderate.

*Propagation type*.—Meristematic tissue culture propagation using the base of the leaves.

*Propagation details*.—The time needed from the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility*.—Plants have not been observed to be susceptible or resistant to pathogens and pests common to *Vanda*.

*Environmental tolerances*.—Adapt to, at least, USDA Zones 11 and 12 and temperatures as high as 40 degrees Celsius; high tolerance to rain; moderate to high tolerance to wind.

Root system:

*General*.—Moderately dense rooting; with aerial roots only.

*Dimensions, mature roots*.—56.2 cm long with a diameter of 0.4 cm, on average.

*Texture*.—Very fleshy; non-fibrous.

*Color*.—Greyed-green, nearest to a mixture of RHS 192C and 192D; root apex is yellow-green, RHS 146D.

Stem:

*Branching habit*.—Monopodial; no lateral branches present.

*Number of primary (main) stems per plant*.—One.

*Number of secondary (lateral) branches per plant*.—None.

*Appearance and shape*.—Circular, formed by the leaf sheaths.

*Length*.—8.4 cm.

*Diameter*.—0.8 cm.

*Internode length*.—0.8 cm.

*Luster*.—Matte.

*Aspect, main stem*.—Near vertical.

*Strength*.—Very strong.

*Color, juvenile*.—Yellow-green, nearest to RHS 145D.

*Color, mature*.—Yellow-green, nearest to RHS 150D.

*Color at internodes*.—Yellow-green, nearest to RHS 150D.

*Pubescence*.—Glabrous.

Foliage:

*Arrangement*.—Distichous.

*Dimensions*.—23.6 cm long, excluding the sheath, and 2.0 cm wide.

*Shape of blade*.—Ligulate; moderately to strongly carinate.

*Aspect*.—Moderately curved.

*Apex*.—Unequal praemorse.

*Base*.—Sheathing.

*Sheath dimensions*.—2.4 cm long and 0.9 cm wide, on average.

*Sheath color*.—Yellow-green, nearest to in between RHS 145B and 145C.

*Margin*.—Entire.

*Pubescence, texture and luster of adaxial surface*.—Glabrous, smooth, and matte.

*Pubescence, texture and luster of abaxial surface*.—Glabrous, smooth, and matte.

*Color*.—Juvenile foliage, adaxial surface — Green, nearest to RHS 143A, and darker towards the apex and the margins, nearest to RHS 137A. Juvenile foliage, abaxial surface — Green, nearest to RHS 143A, and darker towards the apex and the margins, nearest to RHS 137B. Mature foliage, adaxial surface — Yellow-green, nearest to RHS 144A, and suffused with green towards the margins, nearest to RHS NN137B. Mature foliage, abaxial surface — Green, nearest to RHS 143A.

*Venation*.—Parallel.

*Venation color, adaxial surface*.—Yellow-green, nearest to RHS 146A.

*Venation color, abaxial surface*.—Yellow-green, nearest to RHS 144A.

*Petiole*.—No petioles present; leaves sessile.

Inflorescence:

*Inflorescence arrangement*.—Axially placed raceme.

*Natural flowering season*.—Autumn into winter.

*Time to flower*.—Approximately 10 months.

*Flowers per inflorescence*.—Average of 23.

*Flowers per plant*.—18 open flowers and 5 flower buds.

*Inflorescence height*.—Approximately 22.1 cm (measured from base of lowest flower to top of upper flower).

*Inflorescence diameter*.—Approximately 13.2 cm.

*Peduncle*.—Dimensions — Approximately 32.0 cm long and 0.45 cm wide. Aspect — Generally at a 25 degree angle to lateral branch axis. Strength — Moderately strong. Texture and luster — Glabrous and matte. Color — Yellow-green, nearest to RHS 146A; suffused with greyed-purple towards the proximal end, nearest to RHS N186C; and, suffused with a mixture of greyed-orange and greyed-purple towards the distal end, in between RHS 175A and 183A.

Bud:

*Length*.—Average of 1.2 cm.

*Diameter*.—Average horizontal diameter is 1.2 cm; the vertical diameter is 1.6 cm.

*Shape*.—Cubic, with a deltoid apex which is pointed downward.

*Pubescence, texture and luster*.—Glabrous, smooth and matte.

*Color*.—Yellow, nearest to a mixture of RHS 11A and 11B, and lightly suffused with greyed-green at the apex, nearest to RHS 197C.

Flower:

*Flower type*.—Zygomorphic (orchidaceous), typical shape for the genus *Vanda*.

*Flowering habit*.—Moderately free flowering.

*Shape*.—Zygomorphic, single; consisting of three sepals and three petals, one of which is transformed into a labellum; the two lateral petals moderately overlap the lateral sepals and slightly overlap the dorsal sepal; lateral sepals not overlapping.

*Attitude*.—Flowers are outward-facing to slightly nodding.

*Vertical height*.—Approximately 6.1 cm.

*Diameter*.—Approximately 6.0 cm.

*Depth*.—Approximately 2.3 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 2.9 cm. Width — Approximately 2.4 cm. Shape — Broad obovate. Apex — Broad, bluntly acute. Base — Cuneate. Margin — Entire; not undulated to lightly undulated. Pubescence, texture and luster of upper surface — Glabrous, velvety and matte. Pubescence, texture and luster of lower surface — Glabrous, velvety and matte. Color when opening, upper surface — Orange, nearest to RHS 24B, and fading to yellow-orange towards the central portion, nearest to RHS 15B; very slightly suffused with yellow-green at the apex, nearest to RHS 146D; finely dotted with a mixture orange and greyed-orange, in between RHS 26A and 168A. Color when opening, lower surface — Orange, nearest to RHS 24B, and fading to yellow towards the central portion, nearest to RHS 11B; very lightly suffused with yellow-green at the apex, nearest the RHS 146D. Color when fully opened, upper surface — Orange, nearest to RHS 24A, and fading to yellow-orange in the central portion, nearest to RHS 23A; finely dotted greyed-orange, nearest to RHS 169D. Color when fully opened, lower surface — Orange, nearest to RHS 24A, and fading to yellow-orange in the central portion, nearest to RHS 23B. Fading, upper surface — Not fading. Fading, lower surface — Not fading. Venation — Densely reticulate. Venation color, fully opened, upper surface — Orange, nearest to RHS 24A, and fading to yellow-orange in the central portion, nearest to RHS 23B. Venation color, fully opened, lower surface — Yellow-orange, nearest to RHS 23B.

*Labellum*.—Shape — Three-lobed; the shape of the lateral lobes is obovate, and the aspect is involute; the shape of the central lobe is broad oblong, and the aspect is slightly revolute. Length — Central lobe — Approximately 1.1 cm. Lateral lobes — Approximately 0.6 cm. Width — Central lobe — Approximately 0.8 cm; 0.7 at the apex. Lateral lobes — Approximately 0.6 cm. Apex — Central lobe — Straight. Lateral lobes — Obtuse. Base — Central lobe — Cuneate. Lateral lobes — Cuneate. Margin — Central lobe — Entire; not undulated. Lateral lobes — Entire; not undulated. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — Orange, nearest to RHS 26A, and heavily suffused with yellow-green, nearest to a mixture of RHS 152C and 152D. Lateral lobes — Orange, nearest to N25A; base is orange-red, nearest to RHS N34A. Color when opening, lower surface — Central lobe — Orange, nearest to RHS 26A; heavily suffused with yellow-green, nearest to a mixture of RHS 152C and 152D; base is yellow-orange, nearest to 21B. Lateral lobes — Orange, nearest to RHS N25B. Color when fully opened, upper surface — Central lobe — Orange, nearest to RHS 28B. Lateral lobes — Orange, nearest to N25A; base is orange-red, nearest to a mixture of RHS N34A and N34B. Color when fully opened, lower surface — Central lobe — Orange, nearest to 26A; base is yellow-orange, nearest to RHS 21B. Lateral lobes — Orange, nearest to RHS N25B. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities*.—Dimensions — 0.8 cm long and 0.4 cm wide, on average. Color — Orange, nearest to RHS 28B.

*Spurs*.—Quantity — Average of 1. Length — Approximately 0.8 cm. Diameter — Approximately 0.2 cm. Vertical height — Approximately 0.4 cm, at the base. Shape — Oblong; flattened. Apex — Obtuse. Base — Broad cuneate. Pubescence, texture and luster — Glabrous, smooth, and matte. Color — Orange, nearest to RHS 24B.

*Sepals*.—Quantity — Average of 3 unfused sepals. Arrangement — One dorsal sepal and two lateral sepals. Length — Dorsal sepal — Approximately 3.1 cm. Lateral sepals — Approximately 2.9 cm. Width — Dorsal sepal — Approximately 3.0 cm. Lateral sepals — Approximately 3.1 cm. Shape — Dorsal sepal — Broad ovate. Lateral sepals — Reniform. Apex — Dorsal sepal — Obtuse. Lateral sepals — Obtuse. Base — Dorsal sepal — Cuneate. Lateral sepals — Cuneate. Margin — Dorsal sepal — Entire; no undulation to lightly undulated. Lateral sepals — Entire; no undulation to lightly undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Yellow-orange, nearest to RHS 23B, and fading to yellow-orange towards the central portion, nearest to RHS 15B; very slightly suffused with yellow-green at the apex, nearest to RHS 146D; finely dotted greyed-orange, nearest to RHS 168C. Lateral sepals — Orange, nearest to RHS 24B, and fading to yellow-orange towards the apex, nearest to RHS 22A; very finely dotted greyed-orange towards the margins, nearest to RHS 168C. Color when opening, lower surface — Dorsal sepal — Yellow-orange, nearest to 20B, and darker towards the margins and apex, nearest to RHS 22A. Lateral sepals — Yellow-orange, nearest to RHS 22A; darker towards the margins and apex, nearest the RHS 23B. Color when fully opened, upper surface — Dorsal sepal — Orange, nearest to a mixture of RHS N25B and N25C, and fading lighter towards the central portion, nearest to RHS 24B; finely dotted with a mixture orange and greyed-orange, nearest to RHS 26B and 168C. Lateral sepals — Orange, nearest to RHS 25B, and darker towards the margins and apex, nearest to RHS 25A; very finely dotted with a mixture of orange and greyed-orange towards the margins, nearest to RHS 26B and 168C. Color when fully opened, lower surface — Dorsal sepal — Orange, nearest to a mixture of RHS N25B and N25C, and fading lighter towards the central portion, nearest to a mixture of RHS 23B and 24B; finely dotted with a mixture orange and greyed-orange, nearest to RHS 26B and 168C. Lateral sepals — Orange, nearest to RHS 25B, and darker towards the margins and apex, nearest to RHS 25A. Fading, upper surface — Not fading. Fading, lower surface — Not fading. Venation — Densely reticulate. Venation color, fully opened, upper surface — Dorsal sepal — Orange, nearest to a mixture of RHS N25B and N25C, and fading lighter towards the central portion, nearest to RHS 24B. Lateral sepals — Orange, nearest to RHS 25B, and darker towards the margins and apex, nearest to RHS 25A. Venation color, fully opened, lower surface — Dorsal sepal — Orange, nearest to a mixture of RHS N25B and N25C, and fading lighter towards the central portion, nearest to a mixture of RHS 23B and 24B. Lateral sepals — Orange, nearest to RHS 25B, and darker towards the margins and apex, nearest to RHS 25A.

*Pedicels*.—Length — Approximately 4.0 cm. Diameter — Approximately 0.3 cm. Angle — Approximately 85 degree angle to peduncle axis. Strength — Moderate. Texture — Glabrous, axially angled with 5 "ribs", axially twisted (due to resupination). Luster — Glossy. Color — Yellow-green, nearest to RHS 151D but lighter.

*Bract*.—Quantity — One bract present at the base of each pedicel. Shape — Broad oblong; folded around the base of each pedicel. Dimensions — Average of 0.6 cm long and 0.55 cm wide. Apex — Broad obtuse. Base — Broad cuneate. Margins — Entire. Color, inner surface — Brown, nearest to RHS 200C. Color, outer surface — Brown, nearest to RHS 200C.

Reproductive organs:

*Column*.—Length — Approximately 0.4 cm. Diameter — Approximately 0.5 cm. Color — Orange, nearest to RHS 24A; apex is brown, nearest to RHS 200B.

*Ovary*.—Position — Inferior. Diameter — Approximately 0.15 cm. Color — Yellow-green, nearest to a mixture of RHS 150C to 150D.

*Pollinia color*.—Yellow, nearest to RHS 11B.

Seed and fruit: No fruit and seed production has been detected to date.

COMPARISON WITH THE PARENT PLANTS

Plants of the new cultivar 'SPCDW1701' differ from the *Vanda* seed parent, 'BG' (not patented), by the characteristics described in Table 1.

TABLE 1

| Characteristic | 'SPCDW1701' | 'BG' |
|---|---|---|
| Plant vigor. | More vigorous than 'BG'. | Less vigorous than 'SPCDW1701'. |
| Plant size. | Larger than 'BG'. | Smaller than 'SPCDW1701'. |
| Flower size. | Larger than 'BC'. | Smaller than 'SPCDW1701'. |
| Number of flowers per inflorescence. | Fewer flowers. | More flowers. |
| General coloration of the petals and sepals (excluding the overlaid color pattern) when fully opened. | Lighter orange. | Darker orange. |

Plants of the new cultivar 'SPCDW1701' differ from the *Vanda* pollen parent, *Vanda* 'PK4' (not patented), by the characteristics described in Table 2.

TABLE 2

| Characteristic | 'SPCDW1701' | 'PK4' |
|---|---|---|
| Plant vigor. | More vigorous than 'PK4'. | Less vigorous than 'SPCDW1701'. |
| Plant size. | Smaller than 'PK4'. | Larger than 'SPCDW1701'. |

TABLE 2-continued

| Characteristic | 'SPCDW1701' | 'PK4' |
|---|---|---|
| Flower size. | Smaller than 'PK4'. | Larger than 'SPCDW1701'. |
| Number of flowers per inflorescence. | More flowers. | Fewer flowers. |
| General coloration of the petals and sepals (excluding the overlaid color pattern) when fully opened. | Darker orange. | Lighter orange. |

COMPARISON WITH THE MOST SIMILAR *VANDA* CULTIVAR KNOWN TO THE INVENTOR

Plants of the new cultivar 'SPCDW1701' are most similar to the cultivar, *Vanda* 'SPCDW1204' (European Community Plant Variety Rights grant number 37235). A comparison of 'SPCDW1701' with *Vanda* 'SPCDW1204' is described in Table 3.

TABLE 3

| Characteristic | 'SPCDW1701' | 'SPCDW1204' |
|---|---|---|
| Plant height. | Shorter than 'SPCDW1204'. | Taller than 'SPCDW1701'. |
| Foliage size. | Larger than 'SPCDW1204'. | Smaller than 'SPCDW1701'. |
| Flower attitude. | More outward. | More upright. |
| Flower size. | Smaller than 'SPCDW1204'. | Larger than 'SPCDW1701'. |
| General coloration of the petals and sepals (excluding the overlaid color pattern) when fully opened. | Lighter orange. | Darker orange. |
| General coloration of the central lobe of the labellum. | Lighter orange. | Darker orange. |

That which is claimed is:

1. A new and distinct variety of *Vanda* plant named 'SPCDW1701', substantially as described and illustrated herein.

* * * * *